US010159765B2

(12) United States Patent
Collins et al.

(10) Patent No.: US 10,159,765 B2
(45) Date of Patent: Dec. 25, 2018

(54) TISSUE ENGINEERED DEVICES AND METHODS FOR MAKING SAME

(71) Applicants: Scott Forrest Collins, Austin, TX (US); Thomas Boland, El Paso, TX (US); Maria Yanez, El Paso, TX (US)

(72) Inventors: Scott Forrest Collins, Austin, TX (US); Thomas Boland, El Paso, TX (US); Maria Yanez, El Paso, TX (US)

(73) Assignees: THE BOARD OF REGENTS OF THE UNIVERSITY OF TEXAS SYSTEM, Austin, TX (US); TEVIDO BIODEVICES, Austin, TX (US)

( * ) Notice: Subject to any disclaimer, the term of this patent is extended or adjusted under 35 U.S.C. 154(b) by 99 days.

(21) Appl. No.: 15/031,810

(22) PCT Filed: Oct. 27, 2014

(86) PCT No.: PCT/US2014/062469
§ 371 (c)(1),
(2) Date: Apr. 25, 2016

(87) PCT Pub. No.: WO2015/061800
PCT Pub. Date: Apr. 30, 2015

(65) Prior Publication Data
US 2016/0243286 A1  Aug. 25, 2016

Related U.S. Application Data

(60) Provisional application No. 61/895,840, filed on Oct. 25, 2013.

(51) Int. Cl.
| | |
|---|---|
| *A61F 2/12* | (2006.01) |
| *A61L 27/38* | (2006.01) |
| *A61K 35/28* | (2015.01) |
| *A61K 35/33* | (2015.01) |
| *A61K 35/35* | (2015.01) |
| *A61K 35/44* | (2015.01) |
| *C12N 5/077* | (2010.01) |
| *C12N 5/071* | (2010.01) |
| *A61L 27/22* | (2006.01) |
| *A61L 27/52* | (2006.01) |

(52) U.S. Cl.
CPC ............ *A61L 27/3839* (2013.01); *A61F 2/12* (2013.01); *A61K 35/28* (2013.01); *A61K 35/33* (2013.01); *A61K 35/35* (2013.01); *A61K 35/44* (2013.01); *A61L 27/225* (2013.01); *A61L 27/227* (2013.01); *A61L 27/3804* (2013.01); *A61L 27/3808* (2013.01); *A61L 27/3834* (2013.01); *A61L 27/3886* (2013.01); *A61L 27/52* (2013.01); *C12N 5/0653* (2013.01); *C12N 5/0697* (2013.01); *A61F 2210/0076* (2013.01); *A61F 2220/005* (2013.01); *A61F 2240/004* (2013.01); *A61F 2310/00371* (2013.01); *A61F 2310/00377* (2013.01); *A61F 2310/00383* (2013.01); *A61L 2430/04* (2013.01); *C12N 2502/1352* (2013.01); *C12N 2502/28* (2013.01); *C12N 2533/56* (2013.01); *C12N 2533/76* (2013.01); *C12N 2535/10* (2013.01)

(58) Field of Classification Search
CPC ............................ A61F 2/12; A61F 2002/526
USPC ........................................................ 623/7-8
See application file for complete search history.

(56) References Cited

U.S. PATENT DOCUMENTS

| | | | |
|---|---|---|---|
| 5,824,076 A | 10/1998 | Knowlton | ......................... 623/8 |
| 7,051,654 B2 | 5/2006 | Boland et al. | ................. 101/483 |
| 8,518,396 B2 * | 8/2013 | Van Epps | ............ A61K 8/4926 |
| | | | 424/574 |
| 8,697,059 B2 * | 4/2014 | Van Epps | ............ A61K 8/4926 |
| | | | 424/574 |
| 2002/0159982 A1 | 10/2002 | Bonassar et al. | ............ 424/93.7 |
| 2002/0182241 A1 * | 12/2002 | Borenstein | ............ A61F 2/0077 |
| | | | 424/422 |
| 2004/0237822 A1 * | 12/2004 | Boland | ................. B01L 3/0268 |
| | | | 101/483 |
| 2013/0164339 A1 * | 6/2013 | Murphy | .............. A61L 27/3826 |
| | | | 424/400 |
| 2013/0172995 A1 | 7/2013 | Altman et al. | ..................... 623/8 |
| 2014/0228970 A1 * | 8/2014 | Boland | .................... B05D 5/00 |
| | | | 623/23.72 |
| 2014/0234953 A1 * | 8/2014 | Vacanti | ............... A61L 27/3604 |
| | | | 435/297.1 |
| 2014/0306371 A1 * | 10/2014 | Guenther | ............... C12M 23/16 |
| | | | 264/177.18 |
| 2015/0111239 A1 * | 4/2015 | Collins | ............. B01L 3/502776 |
| | | | 435/29 |
| 2015/0125507 A1 * | 5/2015 | Chen | .................... A61L 27/225 |
| | | | 424/423 |

(Continued)

FOREIGN PATENT DOCUMENTS

| | | | | |
|---|---|---|---|---|
| CA | 2966431 A1 * | 5/2016 | ......... | A61L 27/3604 |
| WO | WO/96/018424 | 6/1996 | | |

(Continued)

OTHER PUBLICATIONS

Partial European Search Report in European Application No. 14855282.1 dated Mar. 31, 2017.

(Continued)

*Primary Examiner* — Suzette J Gherbi
(74) *Attorney, Agent, or Firm* — Norton Rose Fulbright US LLP (57) ABSTRACT

Tissue engineered constructs and methods for fabricating the disclosed constructs are provided. Some of the disclosed tissue engineered constructs are designed to fill a void in the body due to surgical resection, for example from mastectomy or lumpectomy, wounds and the like. Some disclosed constructs comprise one or more projections designed to mimic the appearance of a structural feature when implanted into a host.

2 Claims, 4 Drawing Sheets

(56) References Cited

U.S. PATENT DOCUMENTS

| | | | |
|---|---|---|---|
| 2015/0212071 A1* | 7/2015 | Berry | G01N 33/5011 435/1.1 |
| 2016/0243286 A1* | 8/2016 | Collins | A61K 35/35 |
| 2016/0282338 A1* | 9/2016 | Miklas | C12M 21/08 |
| 2016/0287756 A1* | 10/2016 | Lewis | B29C 64/40 |
| 2017/0009194 A1* | 1/2017 | Golway | C12M 29/10 |
| 2017/0087590 A9* | 3/2017 | Boland | B05D 5/00 |
| 2017/0130192 A1* | 5/2017 | Retting | C12N 5/0062 |
| 2017/0216498 A1* | 8/2017 | Kang | A61L 27/44 |
| 2017/0232148 A1* | 8/2017 | Nguyen | A61L 27/52 514/180 |
| 2017/0285003 A1* | 10/2017 | Hamilton | G01N 33/5011 |
| 2017/0294017 A1* | 10/2017 | Yuan | G06T 7/0012 |
| 2017/0296322 A1* | 10/2017 | Vacanti | A61L 27/3604 |
| 2017/0355940 A1* | 12/2017 | Neumann | C12M 3/04 |
| 2017/0370908 A1* | 12/2017 | Dauth | C12N 5/0062 |

FOREIGN PATENT DOCUMENTS

| | | | |
|---|---|---|---|
| WO | WO/04/039248 | 5/2004 | |
| WO | WO/06/004951 | 1/2006 | |
| WO | WO/06/112684 | 10/2006 | |
| WO | WO/08/148026 | 12/2008 | |
| WO | WO/12/040408 | 3/2012 | |
| WO | WO 2018022691 A1 * | 2/2018 | A61B 17/00 |

OTHER PUBLICATIONS

Zhu, et al., "Adipose and mammary epithelial tissue engineering" Biomatter. 3:3, e24630, 2013.
Halbleib, et al., "Tissue engineering of white adipose tissue using hyaluronic acid-based scaffolds. I: in vitro differentiation of human adipocyte precursor cells on scaffolds" Biomaterials. 24(18):3125-32, 2003.
Chao, et al., J Card Surg. 18:500-03, 2003.
Flynn, et al., Organogenesis 4(4):228-351, 2008.
Hariprasad, et al., Arch Opthalmol. 129(29):322-35, 2011.
Huss, et al., Scand J Plast Reconstr Surg Hand Surg. 36(3):166-71, 2002.
International Preliminary Report on Patentability in International Application No. PCT/US2014/062469 dated Nov. 4, 2015.
International Search Report in International Application No. PCT/US2014/062469 dated Apr. 16, 2015.
Katz, et al., Clin Plast Surg. 26(4):587-603, 1999.
Patel and Mikos, J Biomater Sci Polym Ed. 15(6):701-26, 2004.
Peer, Am J Surg. 92(1):40-7, 1956.
Zehr, et al., Ann Thorac Surg. 84:1048-52, 2007.

* cited by examiner

TISSUE ENGINEERED DEVICES AND METHODS FOR MAKING SAME

CROSS-REFERENCE TO RELATED APPLICATIONS

This patent application is a national phase application under 35 U.S.C. § 371 of International Application No. PCT/US2014/062469 filed on Oct. 27, 2014, which claims a priority benefit under 35 U.S.C. § 119(e) from U.S. Provisional Patent Application No. 61/895,840 filed on Oct. 25, 2013. The entire contents of each of the above-referenced disclosures are specifically incorporated herein by reference without disclaimer.

STATEMENT REGARDING FEDERALLY FUNDED RESEARCH

This invention as made with government support under Grant No. IIP-1248451 awarded by the National Science Foundation. The government has certain rights in the invention.

FIELD

The disclosed embodiments relate to tissue engineering. Certain embodiments also relate to cell printing technology or bioprinting. The disclosed embodiments further relate to a tissue engineered construct suitable for implantation and providing volume in the implantation area.

BACKGROUND

Tissue engineering has shown promise for the development of constructs to facilitate large volume soft tissue augmentation in reconstructive and cosmetic plastic surgery (Flynn et al., *Organogenesis,* 4(4), 228-351 (2008)). The treatment of post-operative, congenital or post-traumatic loss of the subcutaneous fat layer can result in scar tissue deformity, and a loss of function (Katz et al., *Clin Plast Surg,* 26(4, 587-603, viii (1999)). Current Clinical Strategies for soft tissue augmentation primarily involve autologous, allogeneic and alloplastic materials. Free fat transfer yields unsatisfactory and unpredictable results, with varying degrees of graft resorption due to a lack of supporting vasculature (Peer, *Am J Surg,* 92(1), 40-7 (1956)). Thus, only small defects can be corrected with injected autologous fat, and even these limited applications require repeated treatments to maintain the desired volume (Huss et al., *Scand J Plast Reconstr Surg Hand Surg,* 36(3): p. 166-71 (2002)).

For the majority of women who undergo reconstruction after a mastectomy, typically the final step in the reconstruction process involves nipple areola complex (NAC) reconstruction. Results of currently available NAC reconstruction techniques are unpredictable; they may lose shape and fade in a few years. Studies highlight that patients with loss of the nipple and areola from cancer continue to experience psychological distress even long after breast mound reconstruction has taken place.

Indications where use of a VFU may be appropriate include without limitation nipple areola reconstruction after the initial nipple areola complex (NAC) is removed during mastectomy; filling the void created from tumor resection such as the indentation formed under the skin after a tumorous tissue is removed, for example but not limited to, melanoma or soft tissue sarcoma, or after a lumpectomy; for constructing features missing or deformed due to congenital defects, for example but not limited to Poland's syndrome and Parry-Romberg syndrome; for filling voids created from injury, disease or trauma such as auto accidents or certain wounds; and cosmetic applications such as lip, breast, or calf augmentation, buttock implant, cheek and other facial implants.

Thus, there is a need for tissue engineered devices suitable for dimensionally filling a void or defect in a mammal, such as the result of surgical resection, wounds or other traumatic injuries, a birth defect, or certain other malformations.

A fundamental challenge in the field of Tissue Engineering is the formation and culture of thick tissue engineered constructs. Thick constructs, on the order of several millimeters to centimeters, are often needed to replace or repair clinically relevant defects. In culture, however, nutrient perfusion is typically limited to a few hundred um in constructs with high cellular density. Highly metabolic cell structures will begin to starve unless nutrient exchange can be facilitated (Patel and Mikos, *J Biomater Sci Polym Ed.,* 15(6):701-26 (2004)). In living organisms the nutrient exchange is handled by the host's vasculature, using blood to supply oxygen and nutrients, and to remove $CO_2$ and waste products. In the lab, an easy alternative to complex vasculature is desired to allow thick tissues to be produced.

Thus, there is also a need for tissue engineered devices with appreciable thickness for repairing of clinically relevant defects and certain cosmetic applications.

SUMMARY

The present teachings are directed to tissue engineered constructs and methods for making such constructs. In certain embodiments, the tissue engineered constructs are useful for implanting into a mammal and when implanted, fill a void that previously existed in the vicinity of the incision or other implantation method. In certain embodiments, the tissue engineered constructs are volume forming units.

A "tissue engineered construct" or "TEC" is a three dimensional device comprising cells, scaffolding and optionally other materials, such as nutrients and growth factors. TECs are based on a manmade or computer rendered design, i.e., not merely a tissue or part of tissue removed from a mammal, such as a human. Nonlimiting examples include TECs comprising a scaffold, and relevant cell types organized in the structure of the desired tissue or organ, with or without a vascular network or primordial vascular network.

A "volume forming unit" or "VFU" is a TEC with a primary purpose of dimensionally filling a void or defect in a human or animal. VFUs may be customized for dimensionally creating or enhancing a structure in a human or animal following implantation.

As TECs increase in size in the third dimension (i.e., the smallest dimension), the need to supply nutrients to, and remove waste products from, interior cells becomes more critical, both in vitro and once implanted in a human or animal host. To address this need, the instant application provides methods for creating thin layers of tissue engineered material that are suitable for being assembled into a TEC, for example without limitation, prior to implanting into a mammal.

According to the current teachings, one or more thin layers of tissue engineered material, sometimes referred to as a thin TEC layer or "TTECL", are prepared and subsequently combined to form a TEC of increased thickness. In certain embodiments, a multiplicity or TTECLs are created and then combined, for example by adhering two or more juxtaposed TTECLs together. In some embodiments, a single TTECL is created and then folded back on itself at least once so that at least two portions of the single TTECL may be combined using a biocompatible adhesive to create at least a two layer TEC. In some embodiments a single TTECL is folded back on itself multiple times and at least some of the opposing portions of such folded TTECL are combined with biocompatible adhesive to create a TEC comprising three or more layers. In some embodiments, one or more TTECL are placed in an incubator to allow the cells and in certain embodiments, the scaffold, comprising the TTECL to develop prior to forming a multilayer TEC. In other embodiments, one or more TTECL is used within a short period after it is created.

Individual TTECLs may be formed by any method utilized to form a tissue. Three nonlimiting examples are: 1) adding a pre-polymerized hydrogel, cells, and other factors into a petri dish and adding an initiator (soluble, light radiation, etc.) to polymerize the cells and factors in situ. A second nonlimiting example comprises bioprinting the TTECL using known techniques. Here the bioprinted TTECL may, itself, have many "layers" or strata due to using an iterative bioprinting process. According to the current teachings, a bioprinted TTECL may be fabricated in one bioprinting process; or a bioprinted TTECL may be incubated after one or more bioprinting steps and additional bioprinted layers are added to such construct after a suitable incubation period. A third nonlimiting example comprises combining one or more cell types with a pre-formed or forming scaffold, optionally followed by incubation. It is to be understood that such TTECL may be as complex or simple as desired.

Aspects of the present disclosure include TECs comprising adipocytes, endothelial cells, fibroblasts, mesenchymal stem cells, and combinations thereof. Preferably such cells are from the same species as the implant is intended for, i.e., allogeneic cells. Most preferably, cells for use in fabricating a TEC for implantation into a host are obtained from that host, i.e., autologous cells. One exemplary source of autologous cells for use in the disclosed TECs and methods of fabricating such TECs are autologous lipoaspirates, such as obtained during a liposuction procedure. Certain disclosed tissue engineered constructs comprise endothelial channels. In certain embodiments, endothelial cells are bioprinted to create aligned endothelial channels. Some TECs comprise at least one projection that is engineered to mimic or simulate the structural appearance of an area on or in a mammal that is needs to be enhanced or reconstructed. In some embodiments, at least one such projection is engineered to mimic or simulate at least one structural feature of a mammalian nipple, for example but not limited to, a human nipple. Certain VFU constructs further comprise a second projection that is engineered to mimic or simulate the structural appearance of a mammalian areola, for example but not limited to, a human areola. Certain such embodiments further comprise at least one projection that is engineered to mimic at least one structural feature of a mammalian nipple circumscribed by a second projection that is engineered to mimic at least one structural feature of a mammalian areola. Typically, such second projection circumscribes the first projection to provide a construct that mimics the structural appearance of a mammalian NAC. Those skilled in the art will appreciate that when VFUs comprising a projection that is engineered to mimic a nipple or comprising two projections that are engineered to mimic an NAC will be useful for implanting into patients undergoing breast reconstruction. VFUs can also be implanted in other areas in a host where a vascular supply is available.

According to certain embodiments, TECs of the present teachings are fabricated using at least one mold, for example without limitation, a negative mold in which a TEC is created using (a) one or more solutions that collectively comprising cells and components suitable for forming a hydrogel or non-hydrogel scaffold, (b) bioprinting, preferably ink-jet printing, or (c) both. For example, without limitation, where a first solution comprising at least one biocompatible hydrogel material is added to a mold and the second solution comprising cells is added to the mold by bioprinting, and wherein the second solution typically comprises at least one biocompatible hydrogel material. In some embodiments, a solution comprising cells and biocompatible hydrogel material is added to the mold, either as a single solution or two solutions added simultaneously. In other embodiments, two solutions are added sequentially in any order, wherein the first solution comprise a first biocompatible hydrogel material, the second solution comprises a second biocompatible hydrogel material, and preferably at least one of the two solutions further comprises cells. In some embodiments, an endothelial channel is fabricated using bioprinting. According to certain embodiments comprising bioprinting, the bioprinting comprises adding cells in a defined pattern to a construct layer, a biocompatible hydrogel, or other scaffold structure. Certain method embodiments comprise placing layers of tissue engineered cells, such as TTECLs, in juxtaposition and binding them together. In some embodiments, the binding comprises using a biocompatible adhesive.

In certain embodiments, multilayer TECs are disclosed. Also disclosed are exemplary methods for creating such multilayer constructs. In certain embodiments, a multiplicity of tissue engineered construct layers are individually fabricated and at least two such construct layers are affixed together in juxtaposition using a biocompatible adhesive. Exemplary biocompatible adhesives include without limitation, certain biological substances such as fibrin glue or it's primary active components fibrinogen and thrombin or another suitable fibrinogen activator, gelatin, collagen, and albumin, including synthetic biologically active analogs of each of these, albumin-glutaraldehyde glue (Chao et al., *J. Card. Surg.,* 18: 500-03 (2003), Zehr, *Ann. Thorac. Surg.* 84:1048-52 (2007)), and certain polyethylene glycol compositions (Hariprasad, *Arch. Opthalmol,* 129: 29, 322-25 (2011). In some embodiments, construct layers are fabricated using bioprinting. In some embodiments, construct layers are fabricated using at least one solution comprising at least one component for forming a hydrogel. In some embodiments, construct layers are fabricated using at least two solutions, wherein at least one of the two solutions comprises at least one of adipocytes, endothelial cells, fibroblasts, or mesenchymal stem cells.

In certain embodiments, construct layers are formed by adding to a substrate, such as a suitable scaffold or prepolymerized scaffold, a first solution comprising adipocytes and either fibrinogen or thrombin, but not both. A second solution comprising endothelial cells and either thrombin or fibrinogen, but not both, is then added to the first solution, in bulk or at a precise location using, for example, a bioprinter. The skilled artisan will appreciate that for a fibrin hydrogel to form, one such solution will comprise fibrinogen and the other solution will comprise thrombin and/or another fibrinogen activator, so that when the two solution are combined, for example without limitation, by overlaying a first solution, combining at least two solutions, or projecting droplets of a second solution with or into a first solution. It is to be appreciated that the designations first and second solutions are for clarity and not intended as a limitation, for example a solution comprising fibrinogen but not thrombin may be deposited on a substrate or in a mold and combined with a solution comprising thrombin but not fibrinogen or vice versa. Likewise, either solution may comprise adipocytes, endothelial cells, or both adipocytes and endothelial cells. The skilled artisan will also appreciate that relatively small amounts of fibrinogen in a solution comprising thrombin, or vice versa, is within the scope of the current teachings provided that such small amounts do not trigger appreciable hydrogel formation prematurely or otherwise make such solution too difficult to manipulate due to increased viscosity. According to certain embodiments, one or more cell type can be added to a first or second solution using bioprinting. In certain embodiments, bioprinting is performed so that the printed cells are added in a pre-determined or defined pattern. In one non-limiting example, endothelial cells may be added in a defined pattern to allow aligned endothelial channels to be formed in the tissue engineered construct.

According to certain embodiments construct layers are formed by adding a solution comprising cells, fibrinogen and thrombin to a substrate and the substrate is incubated under conditions suitable for fibrin formation. In certain embodiments, cells may comprise at least one of adipocytes, endothelial cells, fibroblasts, or mesenchymal stem cells. In some embodiments, a substrate comprising a solution comprising endothelial cells, thrombin, and fibrinogen is incubated to allow endothelial channel formation, regardless of whether the solution is deposited in a single step or in multiple steps, such as overlaying one solution with another solution. The skilled artisan will appreciate that certain fibrinogen activators may be employed with or instead of thrombin to cause fibrin to form and that use of a fibrinogen activator instead of or in addition to thrombin is within the scope of the current teachings.

These and other features of the present teachings are set forth herein.

BRIEF DESCRIPTION OF THE DRAWINGS

The skilled artisan will understand that the drawings, described below, are for illustration purposes only. These figures are not intended to limit the scope of the present teachings in any way.

FIG. 3 illustrates an exemplary method for fabricating a TEC comprising using a positive and a negative mold. The arrowheads point to the projection designed to mimic the structural appearance of a nipple. The arrows point to the projection designed to mimic the structural appearance of the areola.

FIG. 3A is a computer generated 3-D representation of the desired VFU structure used in fabricating the positive mold shown in FIG. 3B.

FIG. 3B is a picture of a positive mold.

FIG. 3C is a picture of an agarose negative mold comprising two projections, one designed to simulate the structure of a nipple and a second projection designed to simulate the structure of an areola. The negative mold was fabricated using the positive mold of FIG. 3B.

FIG. 3D is a picture of a pair of VFUs, each comprising projections designed to simulate the structural features of a NAC. These NACs were fabricated using a negative mold and implanted into the back of a mouse.

FIG. 3E is picture that shows visible contours in the back of the mouse in which the VFUs were implanted seven days after the VFUs were implanted.

FIG. 4A is a picture of a thin section stained with perilipin stain. The arrowheads point to some stained adipocytes. FIG. 4B is a picture of an adjacent thin section stained with a CD-31 stain. The arrows point to some lumens. Scale bars indicate 100 micron distance.

DETAILED DESCRIPTION

It is to be understood that both the foregoing general description and the following detailed description are exemplary and explanatory only and are not intended to limit the scope of the current teachings.

The instant application provides methods and compositions related to tissue engineered constructs, including but not limited to, constructs designed to add volume at and/or below an incision or insertion site when certain constructs of the present teachings is implanted. For example, constructs designed according to certain disclosed tissue engineering methods that mimic the appearance or a nipple or a NAC when implanted. Also disclosed are methods for fabricating multilayered constructs, for fabricating constructs in a hydrogel scaffolds, and methods comprising bioprinting one or more cell type in or on a construct layer, or a hydrogel or other scaffold.

Definitions

The term "biocompatible adhesive" refers to a composition that (a) is capable of adhering two or more construct layers to one another; (b) is not substantially harmful to cells in such construct layers; and (c) and does not elicit a long-term deleterious response when implanted in a host.

The term "biocompatible hydrogel material" refers to a hydrogel or to certain components that, when combined under suitable conditions, result in hydrogel formation. Further, such biocompatible hydrogel material is not substantially harmful to cells that are combined with or embedded in such material and does not elicit a long-term deleterious response when implanted in a host. Nonlimiting examples of biocompatible hydrogel materials include fibrin, fibrinogen, thrombin, a fibrogen activator, polyethelyne glycol, polylactic acid, lactic acid, polyglycolic acid, polycaprolactone, collagen, gelatin, glycosaminoglycans such as hyaluronic acid, and polysaccharides such as chitosan.

The term "bioprinting" as used herein refers to the use of an automated system to deposit cells, scaffolds, biologically compatible substances, or combinations thereof, in precise locations by computer control. Exemplary bioprinters include without limitation, thermal or piezoelectric inkjet bioprinters, extrusion based bioprinters, laser induced forward transfer (LIFT) based bioprinters, syringe pumps, and automated liquid handling systems (see, e.g., Maria et al., *Polym. Adv. Technol.,* 24: 895-902 (2013), Ciu et al., *Biomaterials* 30: 6221-6227 (2009), Boland US 2014/0228970, and Xu et al., U.S. Pat. No. 8,691,274, each of which are hereby incorporated reference in their entirety).

The term "construct layer" as used herein refers to a thin (about 1 mm or less on it's smallest orthogonal dimension) tissue engineered construct that is adhered to or otherwise attached to one or more other construct layers or to an opposing surface of the same construct layer after it has been folded back on itself. A non-limiting example is juxtaposing two construct layers and adding a biocompatible adhesive along all or part of the interface between the two construct layers.

The term "or combinations thereof" as used herein refers to all permutations and combinations of the listed items preceding the term. For example, "A, B, C, or combinations thereof" is intended to include at least one of: A, B, C, AB, AC, BC, or ABC.

The term "endothelial channel" refers to a plurality of endothelial cells (ECs) placed on or in a TEC, in a defined pattern, that can typically sustain blood flow without clotting, and is typically designed to encourage or facilitate more rapid blood flow into the TEC when implanted in a host (human or animal) than if such channels were not provided in the TEC. ECs can be placed in close, three-dimensional proximity to facilitate EC interactions and formation of a vascular lumen. Alternatively, ECs can be positioned in a TEC to facilitate the ECs to connect to the surface of a channel formed by bioprinting or a similar process.

In this application, the use of the singular includes the plural unless specifically stated otherwise. The use of "comprise", "contain", and "include", or modifications of those root words, for example but not limited to, "comprises", "contained", and "including", are not intended to be limiting. The term "and/or" means that the terms before and after can be taken together or separately. For illustration purposes, but not as a limitation, "X, Y and/or Z" can mean "X" or "Y" or "Z" or "X and Y" or "X and Z" or "Y and Z", of "X and Y and Z.".

The section headings used herein are for organizational purposes only and are not to be construed as limiting the described subject matter in any way. All literature and similar materials cited in this application, including patents, patent applications, articles, books, and treatises are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

EXEMPLARY EMBODIMENTS

The following examples provide methods for manufacturing tissue engineered constructs, typically designed to create, restore, or augment one or more superficial body features when an appropriately designed construct is implanted or otherwise inserted on, in, or under the dermis or deeper into the body; and/or to fill a void volume, cavity, or depression resulting from, among other things, surgical resection, wounds, injuries or other trauma, birth defects, wrinkles, the atrophy, wasting, or death of a tissue or organ, or the enhancing the appearance of a scar.

The following examples also provide illustrative tissue engineered constructs fabricated using the methods of the current teachings. The current teachings, having been described above, may be better understood by reference to examples. The following examples are intended for illustration purposes only, and should not be construed as limiting the scope of the teachings herein in any way.

Adipocyte Cell Preparation.

Adipocytes in a tissue culture flask were treated with trypsin for seven minutes, then the flask was scraped with a cell scraper. Trypsin neutralization solution (TNS, Lonza) was added to the cell suspension to neutralize the trypsin, then the cell suspension was centrifuged at 90×g for six min to pellet the cells. After centrifugation, fat floating on the top of the solution was removed. The adipocytes were suspended in 1 milliliter (mL) of fibrinogen solution (60 mg/ml in deionized-water) to make a stock solution. This solution was diluted 2.5×, 5× and 10×; each dilution had a final volume of 1 ml.

It will be appreciated that adipocytes suitable for use in the instant teachings can be obtained from multiple sources. Suitable adipocytes may be obtained from, for example but not limited to, cultured adipocytes, including pre-adipocytes that differentiate into adipocytes, and adipocytes obtained from a lipoaspirate. Adipocytes may be obtained from such lipoaspriates using conventional techniques to obtain fractions enriched for adipocytes. Lipoaspirate derived adipocytes are particularly useful when the lipoaspirate is obtained from the same mammal in which a TEC created using those autologous cells will be implanted. It will also be appreciated that allogeneic cells may be used in TECs and methods disclosed herein although the use of allogeneic cells in the disclosed devices and methods may result in complications with respect to the implanted device.

Endothelial Cell Preparation.

Typically, endothelial cells, cultured in Endothelial Cell Basal Media-2 (EBM-2), were treated with trypsin for four minutes, neutralized with TNS and then the cell suspension was centrifuged at 220×g for five minutes. Cells were counted and mixed with thrombin PBS-calcium solution (50 U bovine plasma thrombin/ml 0.8M $CaCl_2$-PBS, Sigma Chemicals) to achieve a concentration of $4 \times 10^6$ cell/ml.

Scaffolds.

Certain exemplary scaffolds used in the examples below were constructed by bioprinting with a modified inkjet printer. The 'bioink' was a thrombin solution, which in some embodiments, further comprised endothelial cells and/or mesenchymal stem cells. The bioink was printed onto a liquid solution of bovine fibrinogen (Sigma) that had been placed on a substrate. In some cases, the fibrinogen solution further comprised cells, in others it did not.

Confocal Microscopy.

In some of the illustrative examples, some of the exemplary hydrogel constructs were analyzed using confocal microscopy. Typically this was accomplished by placing the gels in Dulbecco's modified phosphate buffered saline (D-PBS) for approximately 10 minutes. The D-PBS was then removed and replaced with D-PBS comprising calcein. Gels were incubated with calcein-DPBS for about 30 min to allow the calcein to penetrate the gels. The gels were then imaged using confocal microscopy to observe three-dimensional patterns of cells in TECs.

Animal Studies.

In some cases, TCEs were implanted in laboratory mice to evaluate biocompatibility and viability of the construct over time.

An incision approximately 2.5 cm long was made in the back of an anesthetized mouse near the tail under aseptic conditions. An adhesion barrier (Seprafilm®) was used to direct vascular ingrowth and anastomosis from the skin only. The adhesion barrier was cut, placed onto a spatula and hydrated with saline solution. Then the adhesion barrier was placed inside of the mouse using the spatula.

The mouse was given a preoperative injection of analgesic 20 minutes prior to the surgical procedure (Buprenorphine 0.1-0.2 mg/kg subQ or carprofen 5 mg/kg). Postoperative analgesia will be with buprenorphine or carprofen every 8 hours for the first two days, as needed.

Figure 1:
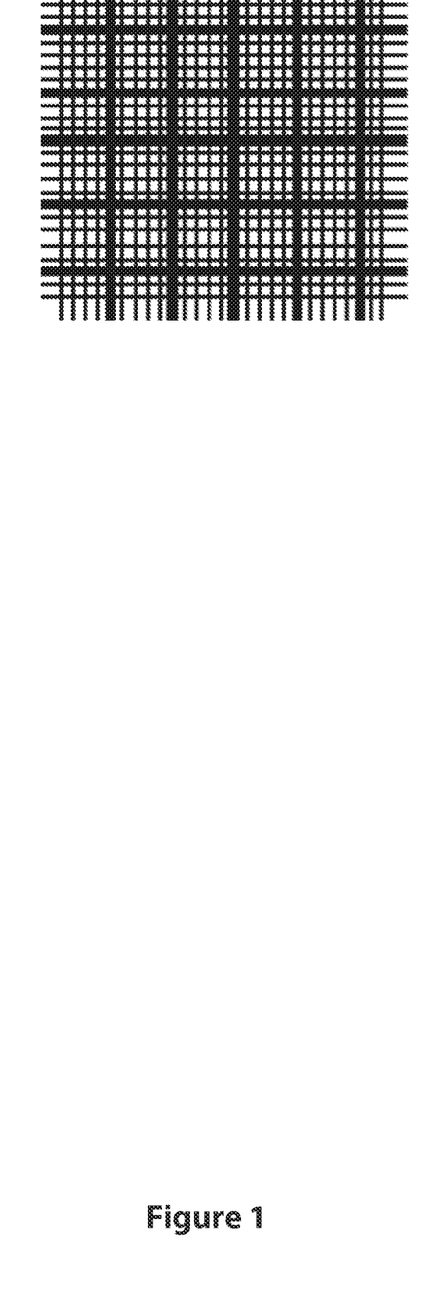
FIG. 1 depicts an exemplary grid or template for bioprinting solutions comprising cells, for example but not limited to ECs and mesenchymal stem cells, on or into a TEC in a defined pattern.

The gel was washed with saline solution and dried using sterile gauze. 50 μL of Fibrinogen solution and 50 μL of thrombin solution were pipetted on one surface of the gel. The formulation of the fibrinogen and thrombin solutions replicated the formulation used in forming the individual TEC layers. The TEC was implanted in the mouse and the incision was sutured closed In one exemplary embodiment, a thrombin solution comprising ECs is printed, using a modified inkjet printer, in a series of lines or channels onto a scaffold or solution comprising fibrinogen in order to polymerize the fibrinogen into fibrin as the cells are added. When the cells are placed into such channels, they could form a microvascular-like lumen which facilitates blood flow after implantation into a host. An exemplary pattern or grid useful for printing a solution comprising ECs onto scaffold, for example, a fibrinogen solution or scaffold (with or without adipocytes) is depicted in FIG. 1.

In this exemplary grid, every fifth line is designed to be larger in order to assess the effects of channel size vs. cellular incorporation. Such defined patterns are typically designed to facilitate printing an appropriate number of ECs per channel, but also to test the ability of potentially larger vascular conduits (shown by the thicker lines) to branch off to smaller conduits (thinner lines) in a way that could allow more rapid vascular infusion.

When ECs are printed or placed in defined patterns according to such grid, the printed ECs are more likely to form an aligned endothelial channel.

Figure 2:
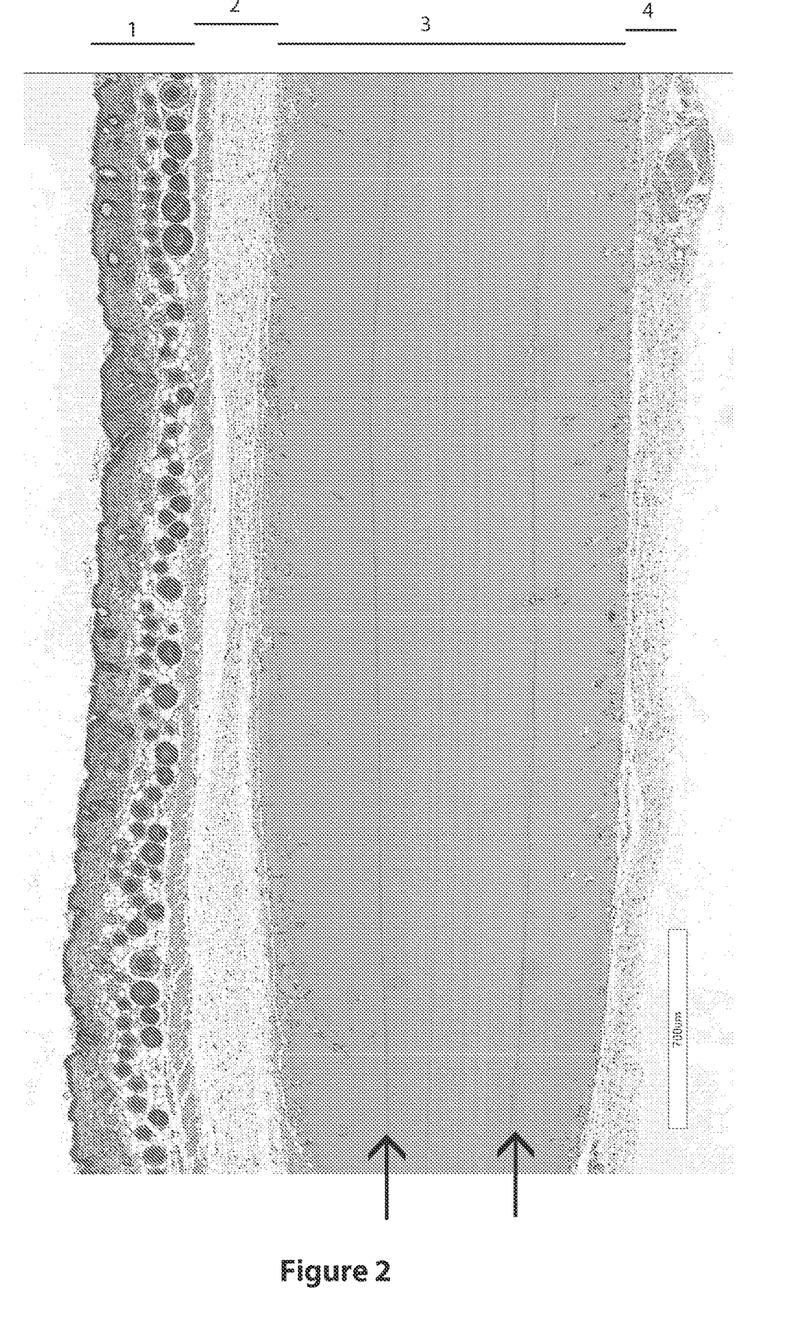
FIG. 2 is a picture of an H&E stained thin section of a multilayer TEC comprising three layers, three weeks after implantation into a mouse. The two arrows on the bottom border point to the interfaces between the three layers of the TEC. The numbers shown in the top margin identify the four histologic sections, the dermis (1), a first layer of inter-connective tissue (2), the TEC implant (3), and a second layer of inter-connective tissue (4). Scale bar indicates 700 microns distance.

In certain embodiments, thick TECs are prepared by combining two or more thin layers of tissue engineered material using a biocompatible adhesive. FIG. 2 is a micrograph of a stained thin section of a fibrin-based "thick" TEC comprising three tissue engineered layers obtained three weeks after implantation in a mouse. The section was stained with hematoxylin and eosin (H&E) according to standard methods. The implanted TEC is the wide band (indicated by "3" at the top or right margin of FIG. 2), bounded on both the top and bottom by layers of connective tissue (indicated by "2" and "4" at the top or right margin of FIG. 2). The implanted TEC appears to be viable as it has maintained its structure for three weeks following implant. The laminated structure of the three layer "thick" TEC is apparent from the two prominent lines (indicated by arrows in bottom or left margin of FIG. 2) seen in the TEC which correspond to the interfaces between (a) the uppermost and middle layers of the construct and (b) the middle and lower layers of construct.

Example 1

Fabrication of TECs Comprising Adipocytes, but not Endothelial Cells

Under aseptic conditions, two hundred and fifty microliter (uL) volumes of fibrinogen solution comprising adipocytes at the various dilutions ($1 \times 10^6$-$10 \times 10^6$ cells/ml) were spotted on glass slides. The thrombin PBS-calcium solution (50 U/ml 0.8M $CaCl_2$-PBS) was then printed onto the slide using a 4×2 cm defined pattern. The pattern on each layer was printed four consecutive times to increase the number of cells and amount of thrombin added to the pattern in the TEC. The printing was performed without moving the TEC during each step to retain the alignment of the printing cells. The slides were incubated for 5 min at room temperature, then the samples were transferred to a incubator for 30 min (37° C. 5% $CO_2$) to allow fibrin hydrogels to form. After 30 minutes incubation, the gels looked opaque, indicating that the fibrin hydrogel scaffolds had formed. In some cases, only the printed pattern appeared opaque, not the entire gel.

Four mL of medium (Dulbecco's modified Eagle's medium (DMEM) with 10% fetal bovine serum (FBS)) was added to 60 mm petri dishes, one for each glass slide. The glass slides were removed from the incubator and the fibrin hydrogel scaffolds were removed from each glass slide and placed in separate petri dishes containing medium.

Example 2

Fabrication of TECs Comprising Adipocytes and Endothelial Cells

Various volumes of fibrinogen solution containing adipocytes at the various dilutions were pipetted on a glass slide (250 μL, 500 μL and 1 mL). A solution of endothelial cells in serum free DMEM ($4 \times 10^6$ cells/ml) was printed using a 4×2 cm grid pattern (1 layer, printed four times). That was followed by bioprinting a thrombin solution (50 U bovine thrombin/ml 0.8M $CaCl_2$-PBS), also using a 4×2 cm grid pattern (1 layer, printed four times). The slides were incubated in the hood for 5 min, then transferred to an incubator (37 C, 5% $CO_2$). Our results suggest that a suitable fibrin gel density is 60 mg/mL.

Example 3

Fabrication of TECs Using Bioprinting

Two 4×6 cm TECs were fabricated using a modified inkjet printer for bioprinting according to a defined pattern for cell placement. The image used to print each layer can be formed in any of several common ways including printing patterns as a "printout" from a word processing program, a sliced rendering from a CAD or conventional or modified 3-D printing program, or from a graphical program such as Adobe Illustrator or Adobe Photoshop. For these bioprinted gels 3 bioprinted layers were formed, one on top of the other. First, 500 μL of fibrinogen solution comprising adipocytes ($10^6$ cells/ml) was pipetted onto a glass slide and spread out over the area of interest. Next, a solution comprising endothelial cells in serum free DMEM ($4 \times 10^6$ cells/ml) and bovine thrombin (50 U/ml 0.8M $CaCl_2$) was printed four consecutive times over the same first bioprinted layer using a 4×2 cm defined pattern. It was printed 4 times to increase the yield of cells and thrombin, but each overprint was performed using the same pattern. Immediately following the last of the four bioprinting runs, 500 μL of the fibrinogen solution comprising adipocytes was pipetted onto the gelled layer and manipulated, if necessary, with the side of a micropipette to assure full coverage. Then the printing step was repeated on the second bioprinted layer to transfer the next pattern onto the second bioprinted layer. Finally, this process was repeated a third time. These steps required 1.5 mL of fibrinogen-adipocyte solution and 80 μL of thrombin-endothelial cell solution. Preferably, each bioprinted layer is incubated for a period of time to assure optimal polymerization prior to the next layer being bioprinted. Incubation can be performed at room temperature or 37 degrees Celsius, or other appropriate conditions.

Example 4

Fabrication of a Custom Shaped VFUs

VFUs, each comprising a NAC, were fabricated using a negative mold. Two VFUs were implanted into the back of a mouse and then explanted after seven days.

The first step in a typical custom TEC fabrication process is forming a computer rendered, volumetric representation of the desired dimensions of the TEC (FIG. 3A). TEC models, such as a NAC, can be formed with varying dimensions (areola major and minor semi-axes, areola thickness, nipple diameter, nipple projection). From the computer representation, a printer readable file is created and a 3D printer is used render the image into a positive mold (shown in FIG. 3B) using standard methods. The mold is washed and sterilized according to standard techniques. Under aseptic conditions, a saline-based agarose negative mold (shown in FIG. 3C) comprising 0.5% to 2% w/v in PBS is formed and then removed from the positive mold. The agarose mold is then transferred to a petri dish followed by the formation of a TEC comprising adipocytes and fibrin. Two exemplary TECs formed using an agarose mold are shown in FIG. 3D. These fibrin-based constructs were implanted subcutaneously in an athymic mouse. The structure of the implanted TEC's surface projections were observable through the skin and remained distinguishable over the 1 week duration of the experiment, as shown in FIG. 3E. Such NACs typically comprise 60 mg/ml fibrinogen, 50 U/ml thrombin, and varying levels of adipocytes, ECs, and mesenchymal stem cells. The arrowheads in FIG. 3 point to the projection that simulates the structural appearance of a human nipple. The arrows in FIG. 3 point to the projection that simulates the structural appearance of a human areola.

Example 5

Figure 4:
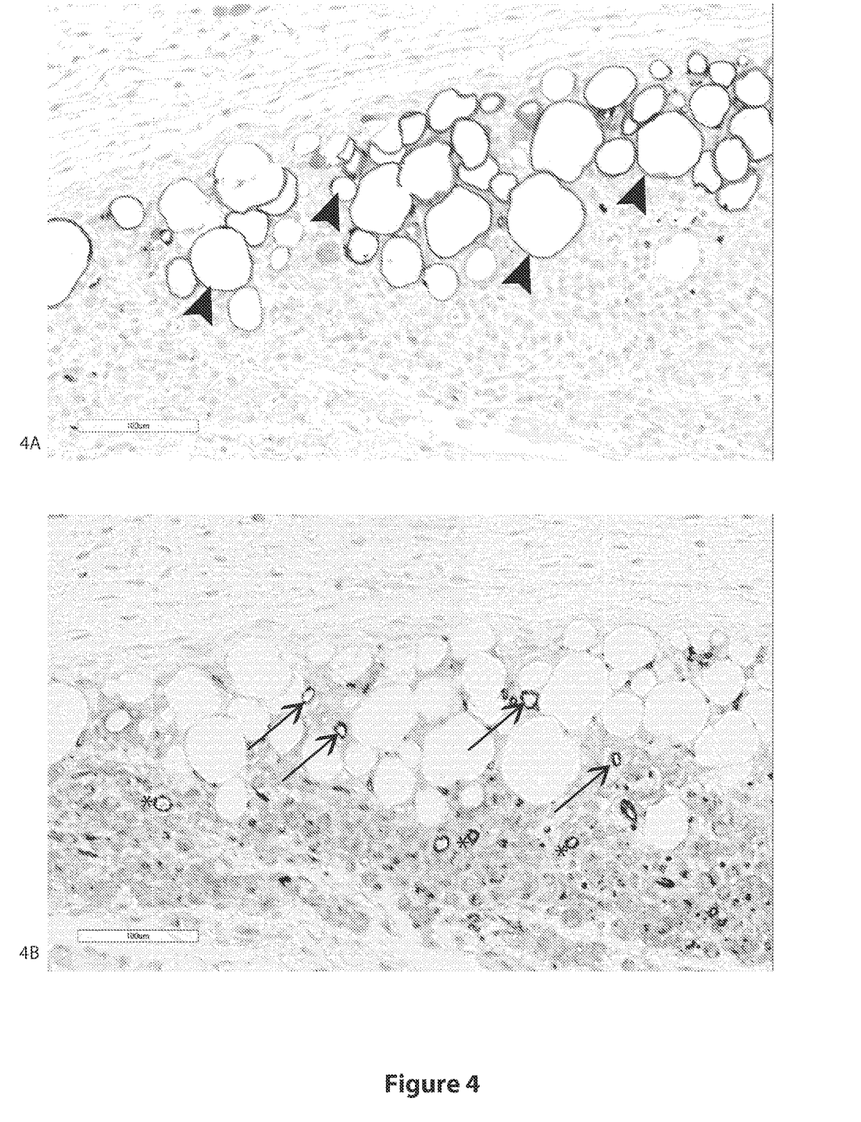
FIG. 4 shows pictures of thin sections obtained from a multilayer TEC that was explanted from a mouse three weeks post implant.

A thick TEC formed from 3 TTECLs each comprising adipocytes, endothelial cells, and mesenchymal stem cells was implanted in an athymic mouse as described. Three weeks post-implant, the TEC and surrounding skin was excised. Thin sections were prepared, stained for markers of adipocytes (perilipin) and endothelial cells (CD-31, PECAM-1), and stained sections analyzed microscopically. FIG. 4A shows adipocytes stained with perilipin can be seen throughout the structure (arrowheads point to some adipocytes). FIG. 4B shows stained endothelial cells (arrows point to some lumens). Some lumens are seen interspersed with cells that stained positive for perilipin (FIG. 4A) and additionally showed hallmarks of adipocytes. Several lumens, highlighted by asterisks, show cells with features of red blood cells, thus suggesting patent blood flow.

Example 6

Customizable TEC for Implantation

It is also envisioned that the TECs disclosed herein may also be fabricated according to disclosed methods in generic forms or shapes that are trimmed to an appropriate size before implantation. In one illustrative embodiment, a thick TEC is prepared from a multiplicity of TTECLs to form a cube or other generic 3-D structure and subsequently trimmed to an appropriate size and shape for implantation.

In one nonlimiting example, TTECLs are fabricated using autologous cells from a patient who will soon have a lumpectomy or other surgical resection procedure. Since the size and shape of the cavity or tissue void created during such a procedure may likely not be known prior to the surgery, fabricating a custom TEC is not practical. Rather, a TEC may be fabricated in a size and shape that is larger than the volume of the expected tissue void, for example a thick TEC fabricated from a multiplicity of TTECLs bound together using a biocompatible adhesive. Alternatively, the multilayer TEC can be fabricated from a single TTECL that is folded back on itself and the overlapping surfaces bound together using adhesive. The thick TEC is transported to operating room and trimmed to fit the void created by tissue removal. Because the tissue and corresponding cell types in the area where the surgery is to be performed is often known in advance, the generic size TEC may be engineered using appropriate cell types, construct density, and endothelial channel density to reflect the composition and properties of the tissue surrounding the surgical site, increasing the chances of a more desirable mechanical and cosmetic clinical outcome.

The tissue engineered constructs and methods of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Although the disclosed teachings have been described with reference to various applications, methods, and compositions, it will be appreciated that various changes and modifications may be made without departing from the teachings herein. The foregoing examples are provided to better illustrate the present teachings and are not intended to limit the scope of the teachings herein. Furthermore, various presently unforeseen or unanticipated alternatives, modifications, variations or improvements therein may be subsequently made by those skilled in the art which are also intended to be encompassed by the following claims. Certain aspects of the present teachings may be further understood in light of the following claims.

What is claimed is:

1. A volume forming unit (VFU) comprising endothelial channels, adipocytes and at least one projection, wherein the at least one projection is designed to simulate at least one structural feature of a nipple.

2. The VFU of claim 1, wherein a second projection is designed to simulate the at least one structural feature of an areola and the second projection circumscribes the at least one projection designed to simulate at least one structural feature of a nipple.

* * * * *